Figure 1:
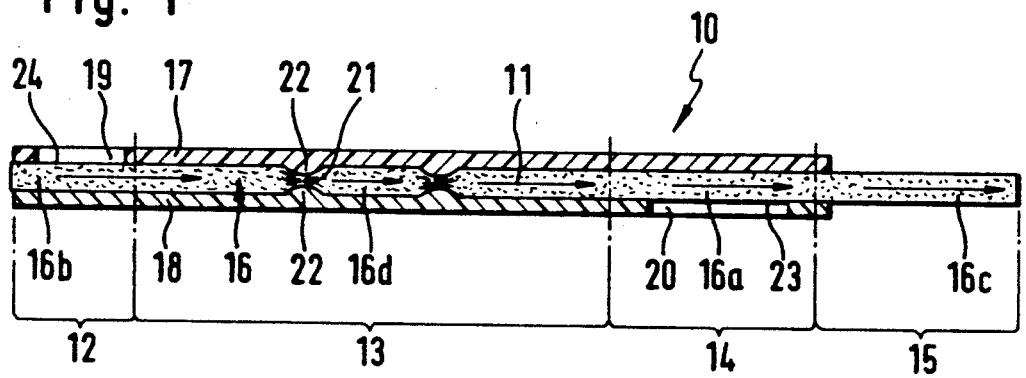

United States Patent [19]

Steinbiss

[11] Patent Number: 5,215,713
[45] Date of Patent: Jun. 1, 1993

[54] TEST KIT FOR DETERMINING AN ANALYTE IN A PASTY SAMPLE

[75] Inventor: Joachim Steinbiss, Lorsch, Fed. Rep. of Germany

[73] Assignee: Boehringer Mannheim GmbH, Mannheim, Fed. Rep. of Germany

[21] Appl. No.: 727,487

[22] Filed: Jul. 9, 1991

[30] Foreign Application Priority Data

Jul. 17, 1990 [DE] Fed. Rep. of Germany ....... 4022655

[51] Int. Cl.$^5$ .................... G01N 21/01; G01N 33/00
[52] U.S. Cl. ......................... 422/61; 422/56; 422/57; 422/58; 435/805; 435/810; 436/66; 436/165; 436/169
[58] Field of Search .......... 422/61, 58, 100, 101, 422/104, 56, 55, 57; 435/810, 805; 436/66, 169, 165, 805, 808

[56] References Cited

U.S. PATENT DOCUMENTS

| | | | |
|---|---|---|---|
| 3,620,677 | 11/1971 | Morison | 422/56 |
| 3,996,006 | 12/1976 | Pagano | 422/58 |
| 4,365,970 | 12/1982 | Lawrence et al. | 422/58 |
| 4,742,002 | 5/1988 | Guadagno | 435/28 |
| 4,789,629 | 12/1988 | Baker et al. | 435/7 |
| 4,965,047 | 10/1990 | Hammond | 422/58 |
| 4,981,786 | 1/1991 | Dafforn et al. | 435/7 |
| 5,004,584 | 4/1991 | Rayman | 422/58 |
| 5,009,846 | 4/1991 | Gavet et al. | 422/56 |
| 5,051,237 | 9/1991 | Grenner et al. | 422/56 |

FOREIGN PATENT DOCUMENTS

| | | |
|---|---|---|
| 0271854 | 12/1987 | European Pat. Off. |
| 0291843 | 5/1988 | European Pat. Off. |
| 0279574 | 8/1988 | European Pat. Off. |
| 0353501 | 7/1989 | European Pat. Off. |
| 0353570 | 7/1989 | European Pat. Off. |

*Primary Examiner*—James C. Housel
*Assistant Examiner*—Long V. Le
*Attorney, Agent, or Firm*—Felfe & Lynch

[57] ABSTRACT

Test kit 10 for determining an analyte in a pasty sample, in particular in stool. It contains a capillary-active fluid transport section 11 which leads from an eluant application zone 12 via a sample application zone 14 to an eluate reception zone 15, together with analysis section containing reagents which react with the analyte and include a component producing a test signal. Improved reliability of the analysis with simplicity of manufacture and ease of handling is achieved by the fact that the fluid transport path 11 between the eluant feed zone 12 and the sample field 23 is formed as a delay section 13. The sample application zone 14 is provided with a sample layer 16a with a sample field 23 for the application of the sample.

11 Claims, 3 Drawing Sheets

TEST KIT FOR DETERMINING AN ANALYTE IN A PASTY SAMPLE

The invention relates to a test kit for determining an analyte in a pasty sample, in particular in stool, comprising a fluid transport section consisting of capillary-active porous material, which leads from an eluant application zone via a sample application zone to an eluate reception zone, and analysis means containing reagents which react with the analyte and include a component producing a test signal. The sample application zone is provided with a sample layer with a sample field for the application of the sample.

Such a test kit is known from published European patent application EP-A-0 291 843. The test kit described there serves, just like the present invention, mainly for the analysis of stool, but can also be used with advantage for other sample materials, in particular homogenates of animal and human tissue samples or galenic suspensions for purposes of pharmaceutical analysis. In general the invention relates to the analysis of pasty, spreadable samples which contain solid constituents, in particular for medical purposes. Discussion will be confined for the sake of simplicity, but without restricting the general import, to the analysis of stool.

The term "test kit" denotes combinations of reagents and adjuvants required for an analysis. Although a test kit consists in most cases of several units, one-piece analysis elements are also available for stool tests, which must likewise be regarded as test kits in the context of the present invention.

The test kit described in the above-mentioned European patent application is suitable in particular for immunological analyses of stool constituents (in particular of HSA, human serum albumin). Compared with the immunological stool tests known to date, it is distinguished above all by ease of handling. The stool sample is placed on the sample field, where it penetrates partially into the porous sample layer. After this an elution fluid (for example, aqueous buffer solution) is applied in the eluant application zone to the fluid transport path, which consists preferably of a single layer material. It chromotographs along the fluid section, eluting soluble constituents out of the sample. The eluate continues to chromatograph in the eluate reception zone on the basis of the capillary forces acting in the fluid transport path. Analysis means are provided there, which react with the analyte and produce a test signal which preferably consists of a colour change. Other test signals (e.g. fluorescence) are also possible, however, depending on the analysis means used.

The object of the present invention is to provide a test kit for the analysis of pasty samples which has improved analytical properties.

The object is achieved with a test kit of the kind described in the preamble by the fact that the fluid transport path is provided with a delay section between the eluant feed zone and the sample field.

Due to the delay section the fluid transport rate in the sample layer is reduced in a controlled manner. If the sample layer is regarded as a separate fluid transport element, the flow rate is determined primarily by the fluid transport properties of its material. On the one hand these are dependent on the capillary forces in the layer, which are determined by the surface properties of the layer material and the size of the capillaries therein, and on the other hand they are determined by the flow resistance in the layer. In practice, however, these parameters cannot be specified and optimized independently of one another. In particular, the layer material also has to be selected according to other critical values such as, for example, strength, relatively small layer thickness (preferably less than 0.5 mm, particularly preferably less than 0.3 mm) and sufficient porosity for the penetration of the sample.

In the case of the previously known test kit the sample field (or in a preferred embodiment the first of a plurality of sample fields) follows immediately downstream the eluant application zone. The flow rate at which the eluant flows through the applied sample in the sample layer is consequently for practical purposes determined only by the latter's own properties. In the case of the present invention the fluid transport rate of the delay section is substantially lower. Since the whole fluid transport path of the test kit forms in close approximation a closed flow path, the flow rate (expressed as mass transfer, for example in $\mu l/sec$) is the same throughout the fluid transport path. The delay section therefrom enables the fluid transport rate within the sample layer in the region of the sample field to be fixed at an optimal value for the particular test independently of the sample layer's own fluid transport properties.

A delay section in the context of the present invention has the property that, considered in isolation, it possesses a lower fluid transport rate for the eluant than the sample layer in the region of the sample field (again considered in isolation). The flow rate in the delay section should preferably be smaller by a factor of at least 2, preferably by a factor of at least 5, than the flow rate in the region of a sample field of the sample layer tested in isolation.

The reduced fluid transport rate in the fluid transport section can be achieved in various ways. In the simplest case the delay section can consist simply of a prolonged section between eluant application zone and sample field (or in the case of several sample fields the first sample field). It is preferably longer than the longitudinal dimension of the sample field in the flow direction, particularly preferably at least twice as long.

The delay section can also consist of a capillary-active layer material which is different from the sample layer and transports the fluid more slowly. This is expensive in manufacturing terms, however, since in this case several layer materials have to be positioned along the fluid transport path and have to be so connected to one another that the fluid can pass over from the one layer into the other ("fluid contact").

Particularly preferred, therefore, is the use of a uniform layer material for delay section and sample layer, with a narrowing being provided in the region of the delay section. The narrowing can consist both of one or more constrictions perpendicular to the superficial extent of the layer material and of one or more sections of the layer material of reduced width.

The various realizations of the delay section can also be combined with one another.

An improved quality of analysis is achieved by means of the invention. The reduced flow rate of the eluant in the sample layer leads to an increase in the analyte concentration. In the context of the present invention it has been established that this is highly advantageous for the analytical quality, although on the one hand highly sensitive reagent systems are available for detecting with extraordinarily high sensitivity the analytes involved, and although on the other the delay section increases the time required for the analysis and necessitates a complicated configuration of the fluid transport path. Due to the fact that, according to the invention, the elution properties are improved and at the same time a relatively insensitive test system is used, the number of false positive findings is considerably reduced and the required detection reliability nonetheless ensured, i.e. false negative findings are largely eliminated.

In addition the invention leads to an improved separation of the colored constituents of the stool which interfere with the analysis.

A particular advantage of the invention consists in the fact that the analysis result is largely independent of the degree of dryness of the sample. Whereas in the case of the previously known analysis elements with a relatively fresh sample the probability of false positive findings rose, or (with reduced detection sensitivity of the analysis system) the probability of false negative findings grew in the case of well dried-out samples, almost the same results are obtained according to the invention with virtually fresh samples and those stored for protracted periods.

Relatively insensitive, non-immunological, in particular enzymatic analyses can also be carried out with great reliability according to the invention.

It is found, surprisingly, that the reduction of the flow rate, although it leads to an enrichment of the analyte, does not lead in practice to a troublesome increase in concentration of the stool constituents interfering with the analysis.

In accordance with the invention, a test kit for determining an analyte in a pasty sample comprises a capillary-active fluid transport path which leads from an eluate application zone via a sample application zone to an eluate reception zone, in which the sample application zone has a sample layer having a sample field for the application of the sample. The test kit also includes analysis means containing reagents which react with the analyte and comprise a component producing a test signal. A section of the fluid transport path between the eluant feed zone and the sample field is formed as a delay section.

For a better understanding of the invention, together with other and further objects thereof, reference is made to the following description, taken in connection with the accompanying drawings, and its scope will be pointed out in the appended claims.

Figure 2:
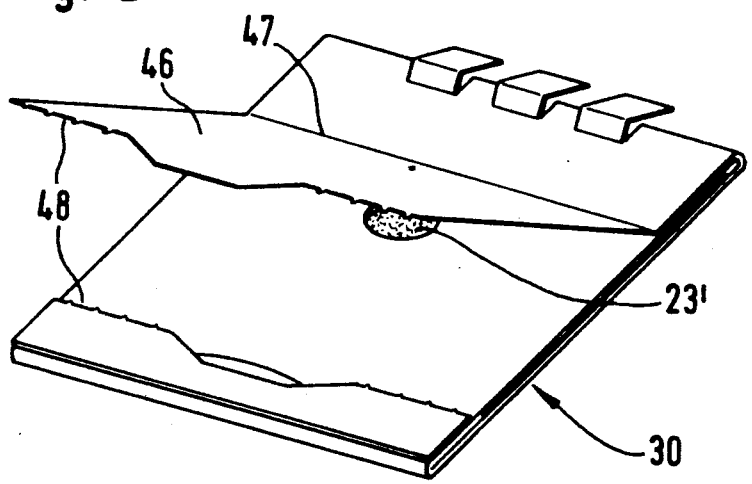
Figure 3:
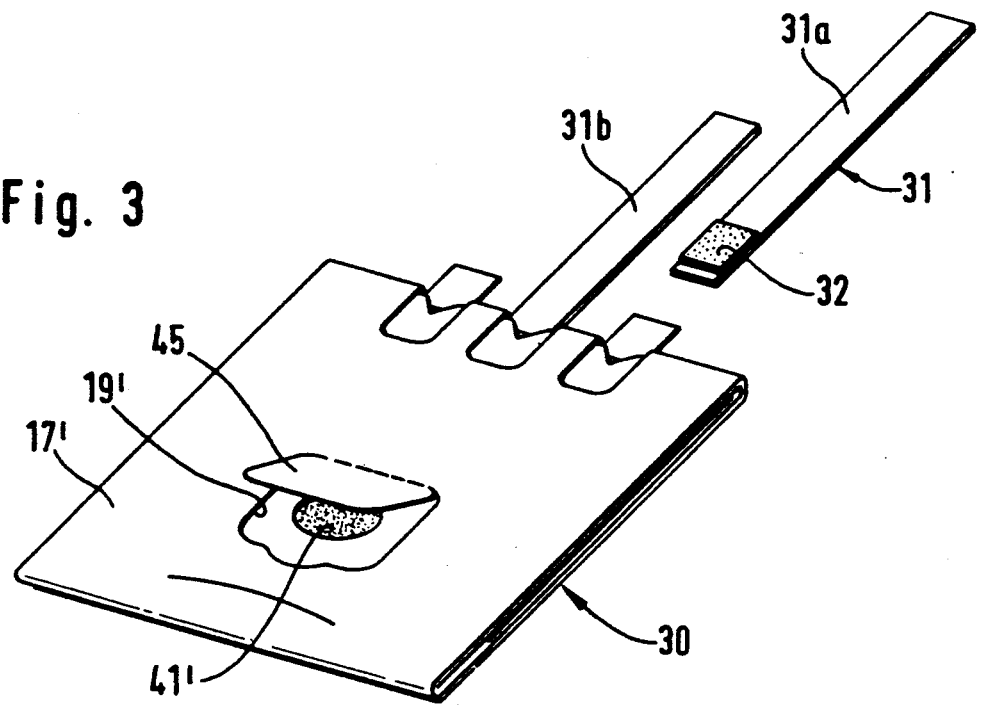
Figure 4:
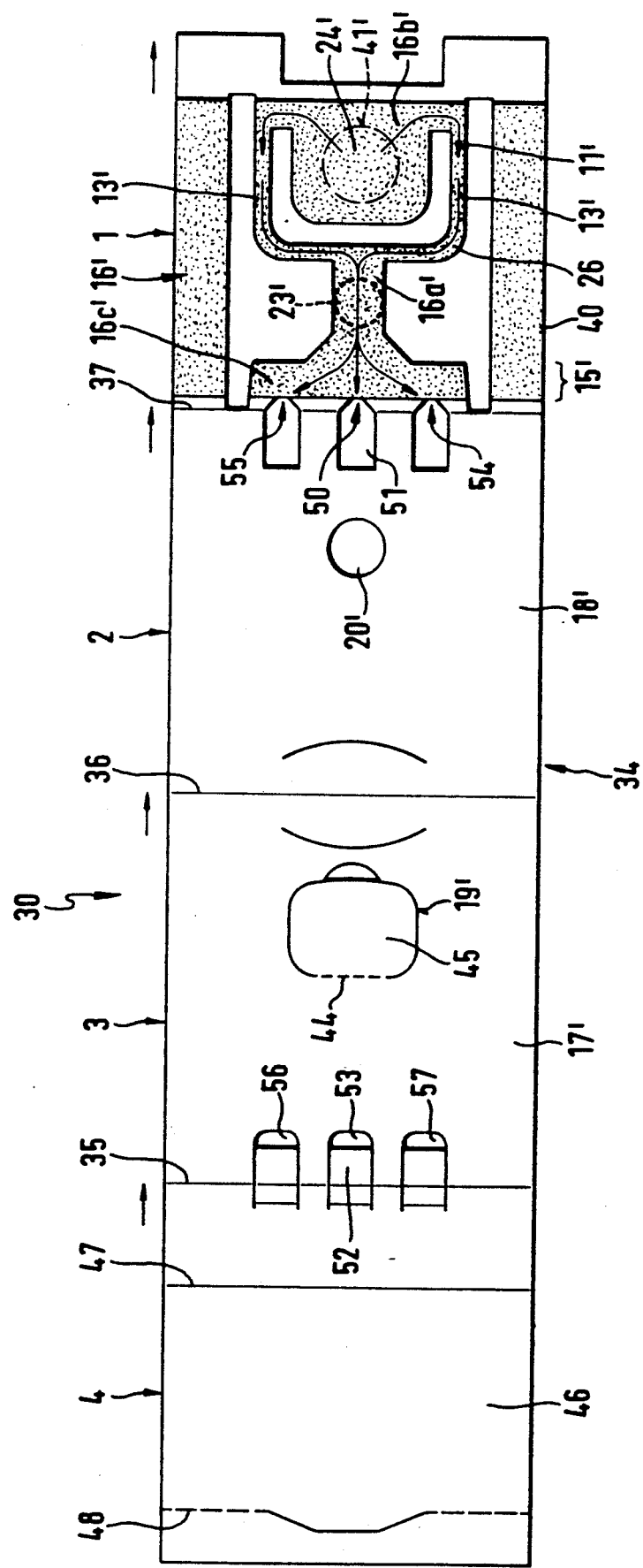
Figure 5:
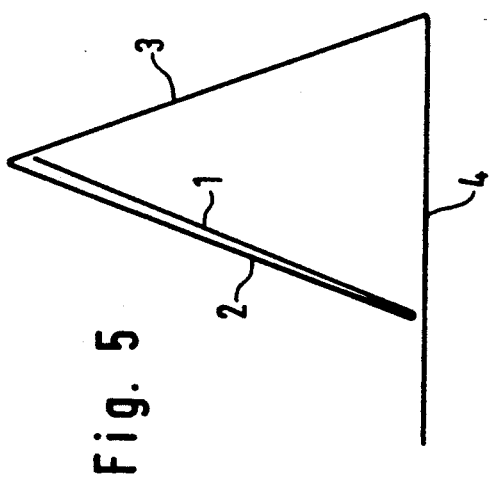
Figure 6:
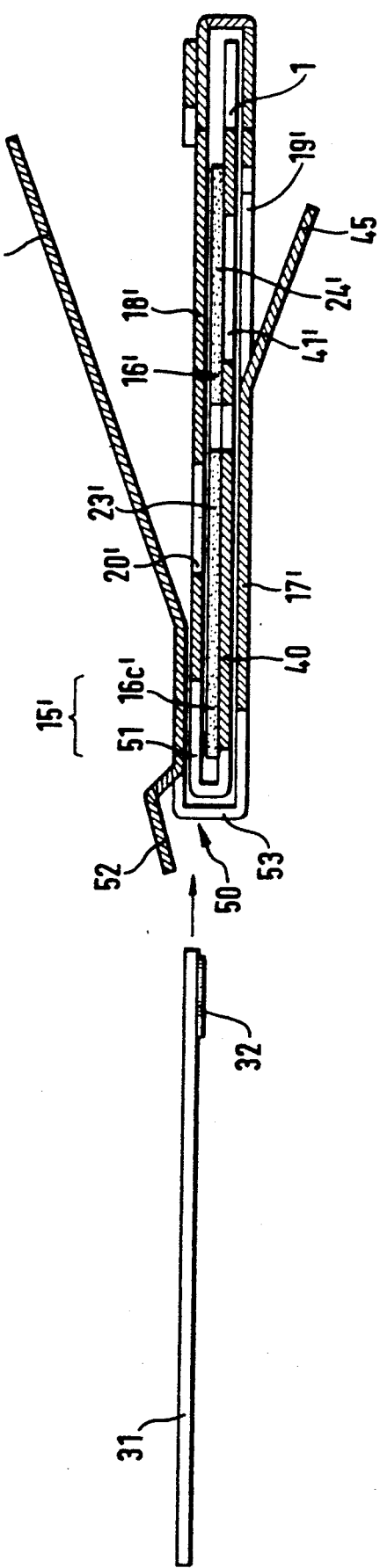

Referring now to the drawings:

FIG. 1 shows an overall view of a test kit according to the invention in cross-section;

FIG. 2 shows the sample collecting unit of a preferred embodiment viewed in perspective from the patient's side, FIG. 3 shows a sample collecting unit as per FIG. 2 viewed in perspective from the doctor's side, including test carriers forming part of the test kit, FIG. 4 is a view of a cardboard blank for manufacturing a sample collecting unit according to FIGS. 2 and 3, FIG. 5 is a folding scheme for FIG. 4, FIG. 6 is a longitudinal section through a sample collecting unit according to FIGS. 2 to 5.

The laboratory model of a test kit 10 shown in FIG. 1 possesses a fluid transport path symbolized by the arrow 11, which leads from an eluant feed zone 12 via a delay section 13 and a sample application zone 14 to an eluate reception zone 15.

The fluid transport path 11 is in the preferred case shown formed from a single continuous insert part 16 consisting of a porous, capillary layer material, which is encased like a sandwich between two cover parts 17 and 18. This embodiment is particularly easy to manufacture. In the context of the invention, however, different layer materials can also be used in the zones 12 to 15, which are in fluid contact with one another. The fluid contact can moreover be produced not only by capillary-active porous layer materials, but also by capillary columns or tubes. The individual sections of the layer material in the zones 12 to 15 are labelled suction layer 16b, delay layer 16d, sample layer 16a and eluate reception layer 16c.

The first cover part 17 and the second cover part 18 possess in each case a recess 19 or 20, through which the fluid transport section is accessible in the eluant application zone 12 (suction layer 16b) or in the sample application zone 14 (sample layer 16a). The cover parts 17, 18 are made of a moisture-proof layer material, for example coated cardboard or a stable plastics film. They can optionally also be manufactured as shaped parts (for example as shown in EP-A-0 291 843).

The delay layer 16d consists in the preferred case shown in FIG. 1 of the same capillary-active flat layer material (of the insert part 16) as the rest of the transport path. Its fluid transport cross-section is narrowed by constrictions 21 at which the layer material is compressed perpendicular to its surface dimension. In addition the delaying effect of the delay section 13 is based on the fact that it is relatively long. Its length preferably is at least 25% of the overall fluid transport path from the eluant application zone 12 to the eluate reception zone 15.

In the case of the embodiment shown the constrictions 21 are fixed by corresponding raised profilings 22 on the cover parts 17, 18. This is only necessary, however, if the material of which the delay layer consists is so flexible that the constrictions 21 do not remain in position without a suitable fixing means.

For the carrying out of an analysis the test kit shown in FIG. 1 is held with the second cover part 18 at the top (i.e. the opposite position to that shown). The sample is applied to the sample field framed by the recess 20, whereby it penetrates partially into the section of the fluid transport path 11 (sample layer 16a) situated beneath it.

For the evaluation the test kit is held with the first cover part 17 at the top, so that an eluant (preferably an aqueous solution containing auxiliary reagents, for example wetting agent and buffer) can be introduced through the recess 19 onto the suction layer 16b situated beneath it. The eluant, which is applied in an amount sufficient to fill the whole capillary-active fluid transport path 11, is transported by capillary forces along the delay section 13 to the sample application zone 14 (sample layer 16a). The flow rate is in so doing slowed down in such a way that it is reduced considerably in the region of the sample layer 16a. A substantially improved elution in the sample application zone 14 is thereby achieved.

In the case of the embodiment shown in FIG. 1 the testing of the analyte takes place by means of the eluate reception layer 16c. The latter can be separated and analysed by means of a reagent set forming part of the test kit. Alternatively the eluate reception layer 16c itself is equipped with the reagents required for producing a test signal specific for the analysis, which is evaluated in a known manner (in the case of a colour change usually by reflection photometry).

FIGS. 2 to 6 show a preferred embodiment which is distinguished both by its operation (accurate and reproducible analysis results) and by simple and therefore inexpensive manufacture.

The test kit includes a sample collecting unit 30 and test carriers 31 which are adapted specifically to the latter (FIG. 3) and are advisably formed similarly to a conventional test strip. They contain in one or more superimposed or adjacent test layers a reagent system for determining a particular analyte. In the figure only one test layer 32 is indicated.

Within a test kit according to the invention use is preferably made of several types of test carriers 31a, 31b, which serve for the determination of different analytes (parameters) and therefore make a profile analysis of the stool possible in a very simple manner. In this way a far more exact diagnostic statement can be made on the existence of a particular condition. It is particularly advantageous that the profile is selective, i.e. that only those parameters have to be determined by the doctor which are required in connection with the suspected diagnosis. Moreover, the analysis is for practical purposes just as easy to carry out as the stool blood tests current today, which are carried out in very large numbers as part of health screening.

The sample collecting unit 30 consists of only two parts, namely a blank designated as a folding part 34 and consisting of water-proof-coated, thin (not more than approx. 500 g/m²) cardboard and a insert part 16' consisting of a porous, capillary layer material (FIG. 4 and FIG. 6). In principle, both natural materials and (preferably) hydrophillic plastics are suitable as capillary layer material, which are processed to produce the capillary-forming structures as papers, mats, fabrics or correspondingly porous and structured films. A mat of hydrophillic plastics fibres is particularly preferred.

The folding part 34 possesses three main folding lines 35, 36 and 37, by means of which four sections 1 to 4 are divided off which are folded for the manufacture of the sample collecting unit 30 in the manner shown in FIG. 5.

The section 1 of the folding part 34 serves mainly as a bearing part 40 for the insert part 16'. The insert part 16' is fixed to the bearing part 40 in such a way that its capillary-active properties are not impaired by the fixing. Point- or strip-wise adhesion at the edge of the insert part 16', for example, is suitable.

The sections 2 and 3 form the second cover part 18' with the recess 20', which frames the sample field 23', and the first cover part 17' with the recess 19', which makes the eluant application field 24' accessible.

This layered structure can be seen most clearly in FIG. 6, in which the thickness of the layers shown is exaggerated. The actual thickness of the layer material of which the folding part 34 is manufactured is preferably less than 0.5 mm, so that a packet with a thickness of less than about 2 mm can be folded out of it.

A preferred configuration of the fluid transport path 11', in particular of the delay section 13', can be seen in FIG. 4. The eluate application field 24' in the suction layer 16b' is relatively extended. From here the fluid transport path 11' leads, via a sub-section 26 divided into two, to the sample layer 16a' with the sample field 23' (indicated by dots in FIG. 4) and from there to an eluate reception layer 16c'. It is characteristic of the preferred embodiment shown that the width of the sub-section 26 (sum of both branches) is less than the width of the fluid transport cross-section in the region of the sample field 23'. It is in addition very long (approx. 50% of the overall fluid transport path). In order nevertheless to make a manageable overall size of the sample collecting unit 30 possible, the fluid transport path 11' exhibits windings, at which the fluid transport direction undergoes a plurality of changes.

The eluant application field 24' is accessible from the doctor's side (FIG. 3) of the sample collecting unit through the recess 19' in the first cover part 17' and a further recess 41' in the bearing part 40'. The recess 19' is sealable with a flap 45 swivellable about a broken line 44.

The sample field 23' is accessible from the patient's side (FIG. 2) through the recess 20' in the second cover part 18'. It is sealable with a flap 46 which is swivellable about a broken line 47. It is closed at its front edge by means of a tear line 48 when the sample collecting unit 30 is not is use.

The eluate reception zone 15' is provided with eluate transfer means designated overall as 50. The eluate transfer means 50 and the test carriers 31 are adapted to one another so that eluate present in the eluate reception region 15' can be transferred onto the at least one test layer 32 of the test carrier.

The eluate transfer means 50 comprise in the case shown the eluate reception layer 16c', a distance recess 51 in the second cover layer 18' and a test carrier opening 53 sealed with a flap 52 when the sample collecting unit 30 is in its initial state. As can be seen from FIG. 6, the dimensions are coordinated with one another so that a test carrier engaging with the distance recess 51 through the opening 53 is with its test field 32 in fluid contact with the eluate reception layer 16c'.

In the preferred case shown the eluate reception layer 16c' is widened so that by means of three eluate transfer devices 50, 54 and 55 fluid contact with three test carriers introduced into the openings 53, 56 and 57 and differing with respect to the analyte for which they are specific can be produced. In this way the determination of an analysis profile from several parameters is possible. A particularly preferred combination includes the following determinations:

1. Conventional test for concealed blood, in particular by means of a haemoglobin-peroxidase test.
2. Immunological determination of HSA as per EP-A-291 843.
3. Determination of leucocytes by an enzymatic test of the leucocyte elastase.

The determination of leucocytes by testing for their elastase activity has been developed for the analysis of urine. The possibility of testing for leucocytes in stool has also already been indicated (EP-A-0 012 957). Although the diagnostic relevance of this test, which in particular can provide useful pointers as to the presence of inflammatory disorders, is undisputed, there is to date no easily manageable and reliable methodology enabling this test to be carried out in practice. A test kit for such a determination is provided by the present invention. It has been shown, surprisingly, that particularly good results with regard to sensitivity on the one hand and selectivity on the other (avoidance of false negative and false positive findings) are achieved if, on the basis of this invention, a relatively high concentration of the analyte in the eluate is ensured and on the other a relatively insensitive leucocyte test is worked with. It has been found that a particularly suitable test procedure is the procedure described in EP-B-0 012 957 including the improvements described in EP-B-0 014

929. The detection limit of the leucocytes is preferably fixed at more than 500 leucocytes/μl, particularly preferably more than a thousand leucocytes/μl.

The carrying out of the analysis is very simple:

The patient introduces the stool sample with a spatula through the recess 20' onto the sample area 23' and closes the flap 46. The sample collecting unit 30 is so constructed that a small quantity of air reaches the sample, so that the latter dries out during storage.

For the testing of the sample the test carrier openings 53, 56 and 57 and the flap 45 sealing the eluant application field 24' are opened. Depending on the desired analysis profile, one or more test carriers are introduced into the eluate transfer devices 50, 54 and 55. A measured amount of eluant is metered onto the eluant application field 24'. The test carrier 31 is removed at a predetermined time and the test signal is evaluated visually or with an apparatus.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A test kit for determining an analyte in a pasty spreadable sample containing solid constituents, comprising:
   an eluant feed zone;
   an eluate reception zone for receiving an eluate liquid;
   a fluid transport path means for transporting a liquid by capillarity in a flow direction which leads from said eluant feed zone via a sample application zone to said eluate reception zone, said sample application zone having a porous sample layer comprising a sample field for the application of the pasty solid containing sample to partially penetrate into the porous sample layer;
   a delay section in the fluid transport path between the eluant feed zone and the sample field, said delay section comprising delay means for controlled reducing of the fluid transport rate in the sample layer and having a fluid transport rate which is smaller by at least a factor of two than the fluid transport rate of the sample layer in the sample field, each of said fluid transport rates being measured in isolation;
   a covering part which covers at least said sample application zone and includes means for providing access to said sample field for the pasty spreadable solid containing sample to be applied to and cover said sample field; and
   analysis means containing reagents which react with the analyte and comprise a component producing a test signal.

2. The test kit of claim 1 wherein the sample field has a longitudinal dimension in the flow direction and the delay section is substantially longer than said sample field in that direction.

3. The test kit of claim 1 wherein the sample layer has a fluid transport cross-section and the delay section comprises a flat layer material for transporting a liquid by capillarity, said delay section having a fluid transport cross-section and comprises a narrowing in which the fluid transport cross-section of the delay section is smaller than the fluid transport cross-section of the sample layer.

4. The test kit of claim 3 wherein the narrowing is a constriction at which the layer material is compressed perpendicular to its surface dimension.

5. The test kit of claim 3 wherein the sample field has a sample layer and the narrowing is a sub-section of reduced width in relation to the sample layer width.

6. The test kit of claim 1, further comprising a sample collecting unit including the fluid transport path and which includes eluate transfer means in the eluate reception zone and in which the analysis means includes a test carrier with at least one test layer, and in which the test carrier and the sample collecting unit are adapted so that eluate present in the eluate reception zone is transferred by means of the eluate transfer means to said least one test layer of the test carrier.

7. The test kit of claim 6 wherein the eluate reception zone comprises a plurality of eluate transfer means each of which is in fluid communication with the fluid transport path.

8. The test kit of claim 1 wherein at least a part of the fluid transport path comprises an insert part including a porous capillary layer material.

9. The test kit of claim 8 wherein the covering part comprises a first cover part and a second cover part, said first and second cover parts encasing the insert part therebetween, and the cover parts having in each of the eluant application zone and the sample application zone means through which the fluid transport path of the insert part is accessible.

10. The test kit of claim 9 further comprising a bearing part of water-proof layer material to which the insert part including porous layer material is fixed, the water-proof layer material being encased between the cover parts together with the insert part.

11. The test kit of claim 1 wherein the analysis means include a reagent system for determining an elastase.

* * * * *